United States Patent
Khong

(10) Patent No.: US 9,827,328 B2
(45) Date of Patent: *Nov. 28, 2017

(54) COMBINATION THERAPY FOR TREATMENT OF CANCER

(71) Applicant: UNIVERSITY OF SOUTH ALABAMA, Mobile, AL (US)

(72) Inventor: Hung T. Khong, Mobile, AL (US)

(73) Assignee: UNIVERSITY OF SOUTH ALABAMA, Mobile, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/055,940

(22) Filed: Feb. 29, 2016

(65) Prior Publication Data

US 2016/0250343 A1 Sep. 1, 2016

Related U.S. Application Data

(63) Continuation-in-part of application No. 14/117,832, filed as application No. PCT/US2012/038111 on May 16, 2012, now Pat. No. 9,308,276.

(60) Provisional application No. 61/487,232, filed on May 17, 2011.

(51) Int. Cl.
| | | |
|---|---|---|
| A61K 38/38 | (2006.01) | |
| A61K 31/337 | (2006.01) | |
| A61P 35/00 | (2006.01) | |
| A61K 47/48 | (2006.01) | |
| A61K 38/19 | (2006.01) | |
| A61K 45/06 | (2006.01) | |
| A61K 31/436 | (2006.01) | |
| A61K 31/675 | (2006.01) | |
| A61K 31/704 | (2006.01) | |

(52) U.S. Cl.
CPC ...... *A61K 47/48284* (2013.01); *A61K 31/337* (2013.01); *A61K 31/436* (2013.01); *A61K 31/675* (2013.01); *A61K 31/704* (2013.01); *A61K 38/193* (2013.01); *A61K 45/06* (2013.01); *A61K 47/48884* (2013.01)

(58) Field of Classification Search
None
See application file for complete search history.

(56) References Cited

U.S. PATENT DOCUMENTS

| 2009/0105329 A1 | 4/2009 | Chiao et al. |
| 2014/0051635 A1 | 2/2014 | Khong |
| 2014/0080760 A1 | 3/2014 | Khong |

FOREIGN PATENT DOCUMENTS

WO    WO 2006/094068    9/2006

OTHER PUBLICATIONS

Agrawal et al., Pathological Complete Response in Triple Negative Poorly Differentiated Invasive Ductal Breast Carcinoma Detected During Pregnancy. J Clin Oncol. (2007) 25: 2616-2620.
Alba et al., Multicenter randomized trial comparing sequential with concomitant administration of doxorubicin and docetaxel as first-line treatment of metastatic breast cancer: a Spanish Breast Cancer Research Group (GEICAM-9903) phase III study. J Clin Oncol. (2004) 22(13): 2587-93.
American Cancer Society: Cancer Facts and Figures 2007. Atlanta: American Cancer Society; 2007; 56 pages.
Bear et al., "Sequential preoperative or postoperative docetaxel added to preoperative doxorubicin plus cyclophosphamide for operable breast cancer:National Surgical Adjuvant Breast and Bowel Project Protocol B-27". J Clin Oncol. May 1, 2006;24(13):2019-27.
Bird A.P., The relationship of DNA methylation to cancer. Cancer Surv. (1996) 28: 87-101.
Bishop et al., Initial paclitaxel improves outcome compared with CMFP combination chemotherapy as front-line therapy in untreated metastatic breast cancer. J Clin Oncol. (1999) 7(8): 2355-64.
Blum et al.; Long-term Disease Control in Taxane-Refractory Metastatic Breast Cancer Treated with nab paclitaxel. 2004 ASCO Annual Meeting Proceedings (Post-Meeting Edition). (Jul. 15 Supplement), (2004) 22(14S): Abstract No. 543; 1 page.
Bonneterre et al., Docetaxel vs 5-fluorouracil plus vinorelbine in metastatic breast cancer after anthracycline therapy failure. Br J Cancer. (2002) 87(11): 1210-1215.
Castagna et al., Pegfilgrastim versus filgrastim after high-dose chemotherapy and autologous peripheral blood stem cell support. Ann Oncol. (2010) 21: 1482-1485 [published online Dec. 11, 2009].
Celgene Corporation, Azacitidine Investigator's Brochure, Version 7. Summit, NJ; Jun. 17, 2010, 212 pages.
Chan et al., Prospective randomized trial of docetaxel versus doxorubicin in patients with metastatic breast cancer. J Clin Oncol. (1999) 17(8): 2341-2354.
Cheetham et al., "SPARC promoter hypermethylation in colorectal cancers can be reversed by 5-Aza-2'deoxycytidine to increase SPARC expression and improve therapy response", Br J Cancer. (2008) 98: 1810-1819.
Chlenski et al., SPARC expression is associated with impaired tumor growth, inhibited angiogenesis and changes in the extracellular matrix. Int J Cancer. (2006) 118(2): 310-316.
Chlenski et al., SPARC enhances tumor stroma formation and prevents fibroblast activation. Oncogene. (2007) 26(31): 4513-4522.
Citron et al., Randomized Trial of Dose-Dense Versus Conventionally Scheduled and Sequential Versus Concurrent Combination Chemotherapy as Postoperative Adjuvant Treatment of Node-Positive Primary Breast Cancer etc. J Clin Oncol. (2003) 21: 1431-1439.
Cleator et al., "Good clinical response of breast cancers to neoadjuvant chemoendocrine therapy is associated with improved overall survival". Ann Oncol. Feb. 2005;16(2):267-72.

(Continued)

*Primary Examiner* — Julie Ha
*Assistant Examiner* — Kristina M Hellman
(74) *Attorney, Agent, or Firm* — Knobbe, Martens, Olson & Bear, LLP

(57) ABSTRACT

The present invention relates to methods and compositions for the treatment of cancer. Some embodiments include methods of treating cancer comprising administering a chemotherapeutic agent associated with albumin, administering a second chemotherapeutic agent; and administering a third chemotherapeutic agent.

22 Claims, No Drawings

(56) References Cited

OTHER PUBLICATIONS

Clinical Trial NCT00748553 [accessed at URL: clinicaltrials.gov/archive/NCT00748553/2008_09_22, available online Sep. 22, 2008]; 3 pages.
Clinical Trial NCT00542191 Phase II Trial of Neoadjuvant Metronomic Chemotherapy in Triple-Negative Breast Cancer, Feb. 23, 2009; [accessed at URL: clinicaltrials.gov/archive/NCT00542191 on Dec. 16, 2014]; 5 pages.
Conte et al., Concomitant versus sequential administration of Epirubicin and Paclitaxel as first-line therapy in metastatic breast carcinoma: results. Cancer. (2004) 101(4): 704-712.
Cresta et al., A randomized phase II study of combination, alternating and sequential regimens of Doxorubicin and Docetaxel as first-line chemotherapy for women with metastatic breast cancer. Ann Oncol. (2004) 15(3): 433-439.
Desai et al., SPARC expression in breast tumors may correlate to increased tumor distribution of nanoparticle albumin-bound paclitaxel (ABI-007) vs taxol. 2004 SABCS. Abstract No. 206, 2 pages.
Desai et al., Increased endothelial transcytosis of nanoparticle albumin-bound Paclitaxel (ABI-007) by gp60-receptors: a pathway inhibited by Taxol. 2004 SABCS, p. S65, Abstract No. 1071.
Desai et al., Increased Antitumor Activity, Intratumor Paclitaxel Concentrations and Endothelial Cell Transport of Cremophor-Free, Albumin-Bound Paclitaxel, ABI-007, Compared with Cremophor-Based Paclitaxel. Clin Cancer Res. (2006) 12(4). 1317-1324.
H/ 29 Desai et al., Nap Technology: A Drug Delivery Platform Utilising Endothelial gp60 Receptor-based Transport and Tumour-derived SPARC for Targeting. Drug Delivery Report—Enabling drug delivery deal making; Winter 2007/2008; pp. 37-41.
Dobrovic et al., Methylation of the BRCA1 gene in sporadic breast cancer. Cancer Res. (1997) 57: 3347-3350.
Fenaux et al., Azacitidine treatment prolongs overall survival and reduces infections and hospitalizations in patients with WHO-defined acute myeloid leukaemia compared with conventional care regimens: an update. Ecancer (2008) 2: 121; 3 pages.
Fisher et al., "Effect of preoperative chemotherapy on local-regional disease in women with operable breast cancer: findings from National Surgical Adjuvant Breast and Bowel Project B-18". J Clin Oncol. Jul. 1997;15(7):2483-93—Abstract Only.
Gabbara et al., The mechanism of inhibition of DNA (cytosine-5-)-methyltransferases by 5-azacytosine is likely to involve methyl transfer to the inhibitor. Biochem J. (1995) 307: 87-92.
Glover et al., Azacitidine: 10 years later. Cancer Treat Rep. (1987) 71(7-8): 737-46.
Gluck et al., Phase II study of nab-paclitaxel, bevacizumab, and gemcitabine for first-line therapy of patients with HER2-negative metastatic breast cancer (MBC). ASCO Annual Meeting Proceedings; J Clin Oncol. (May 2008) 26(15Supp): 1089.
Gradishar et al., Phase III trial of nanoparticle albumin-bound paclitaxel compared with polyethylated castor oil-based paclitaxel in women with breast cancer. J Clin Oncol. (2005) 23(31): 7794-7803.
Gradishar W.J., Albumin-bound Paclitaxel: a next-generation Taxane. Expert Opin Pharmacother. (2006) 7(8):1041-1053.
Gradishar W. et al., "Randomized comparison of weekly or every-3-week (q3w) nab-paclitaxel compared to q3w docetaxel as first-line therapy in patients (pts) with metastatic breast cancer (MBC)". J Clin Oncol, 2007 ASCO Annual Meeting Proceedings. 25 (18S) (Jun. 20 Supplement), 2007: 1032. Abstract Only.
Herman et al., Silencing of the VHL tumor-suppressor gene by Dna methylation in renal carcinoma. Proc Natl Acad Sci U S A. (1994) 91(21): 9700-9704.
Herman et al., Hypermethylation-associated inactivation indicates a tumor suppressor role for p15INK4B. Cancer Res. (1996) 56(4): 722-727.
Hiltunen et al., Hypermethylation of the APC (Adenomatous Polyposis Coli) gene promoter region in human colorectal carcinoma. Int J Cancer. (1997) 70: 644-648.
Hoffman et al., "Pharmacodynamic Aspects of Modes of Drug Administration for Optimization of Drug Therapy", Crit Rev Ther Drug Carrier Syst. (1999) 16: 571-639.
Holmes et al., Comparable efficacy and safety profiles of once-per-cycle pegfilgrastim and daily injection filgrastim in chemotherapy-induced neutropenia: a multicenter dose-finding study in women with breast cancer. Ann Oncol. (2002) 13: 903-909.
Howell et al., "Demethylating Agents in the Treatment of Cancer", Pharmaceuticals. (2010) 3: 2022-2044.
Ibrahim et al., Phase I and Pharmacokinetic Study of ABI-007, a Cremophor-free, Protein-stabilized, Nanoparticle Formulation of Paclitaxel. Clin Cancer Res. (2002) 8: 1038-1044.
Ibrahim et al., Multicenter Phase II Trial of ABI-007, an Albumin-Bound Paclitaxel, in Women with Metastatic Breast Cancer. J Clin Oncol. (2005) 23(25): 6019-6026.
Ito et al., Frequent inactivation of RASSF1A, BLU, and SEMA3B on 3p21.3 by promoter hypermethylation and allele loss in non-small cell lung cancer. Cancer Lett. (2005) 225(1): 131-139.
Jones et al., DNA modification, differentiation, and transformation. J Exper Zoology.(1983) 228(2): 287-295.
Jones et al., Inhibition of DNA methylation by 5-azacytidine. Recent Results Cancer Res. (1983) 84: 202-211.
Jones et al., Cancer epigenetics comes of age. Nat Genet. (1999) 21: 163-7.
Jones et al., Randomized phase III study of docetaxel compared with paclitaxel in metastatic breast cancer. J Clin Oncol. (2005) 23(24): 5542-5551.
Jüttermann et al., Toxicity of 5-aza-2'-deoxycytidine to mammalian cells is mediated primarily by covalent trapping of DNA methyltransferase rather than DNA demethylation. Proc Natl Acad Sci U S A. (1994) 91(25): 11797-11801.
Kaminskas et al., FDA drug approval summary: Azacitidine (5-azacytidine, Vidaza) for injectable suspension. Oncologist. (2005) 10(3): 176-182.
Karpf et al., Reactivating the expression of methylation silenced genes in human cancer. Oncogene. (2002) 21(35): 5496-5503.
Kim et al., Expression of Osteopontin and Osteonectin in breast cancer. J Korean Med Sci. (1998) 13(6): 652-657.
Kaufmann et al., Recommendations From an International Expert Panel on the Use of Neoadjuvant (Primary) Systemic Treatment of Operable Breast Cancer: An Update. J Clin Oncol. (2006) 24(12): 1940-1949; plus Errata in: J Clin Oncol. (2006) 24(19): 3221.
Koblinski et al., Endogenous Osteonectin/SPARC/BM-40 expression inhibits MDA-MB-231 breast cancer cell metastasis. Cancer Res. (2005) 65(16): 7370-7.
Lane et al., The biology of SPARC, a protein that modulates cell-matrix interactions. FASEB J. (1994) 8(2): 163-173.
Ledda et al., The expression of the secreted protein acidic and rich in cysteine (SPARC) is associated with the neoplastic progression of human melanoma. J Invest Dermatol. (1997) 108(2): 210-214.
Ledda et al., Suppression of SPARC expression by antisense RNA abrogates the tumorigenicity of human melanoma cells. Nat Med. (1997) 3(2): 171-176.
Leone et al., DNA methylation and demethylating drugs in myelodysplastic syndromes and secondary leukemias. Haematologica. (2002) 87(12): 1324-1341.
Li et al., Cytotoxicity and mode of action of 5-Azacytidine on L1210 leukemia. Cancer Res. (1970) 30: 2760-2769.
Li et al., Phase specificity of 5-Azacytidine against mammalian cells in tissue culture. Cancer Res. (1970) 30: 2770-2775.
Marcucci et al., Bioavailability of azacitidine subcutaneous versus intravenous in patients with the myelodysplastic syndromes. J Clin Pharmacol. (2005) 45(5): 597-602.
Martin et al., Adjuvant Docetaxel for Node-Positive Breast Cancer. N Engl J Med. (2005) 352(22): 2302-2313.
Mazouni et al., Inclusion of taxanes, particularly weekly paclitaxel, in preoperative chemotherapy improves pathologic complete response rate in estrogen receptor-positive breast cancers. Ann Oncol. May 2007;18(5): 874-880.
McArthur, HL et al., A feasibility study of bevacizumab plus dose-dense doxorubicin-cyclophosphamide (AC) followed by nanoparticle albumin-bound paclitaxel in early-stage breast cancer;

(56) References Cited

OTHER PUBLICATIONS

Clin Cancer Res. May 15, 2011;17(10):3398-407. doi: 10.1158/1078-0432.CCR-10-1969. Epub Feb. 24, 2011.
Merck Manual—Overview of Leukemia at URL: merckmanuals.com/home/blood_disorders/leukemias/overview_of_leukemia.html?qt=Leukemia&alt=sh; accessed Aug. 20, 2014; 3 pages.
Merck Manual Brain Tumors accessed Aug. 21, 2014 at URL: merckmanuals.com/home/brain_spinal_cord_and_nerve_disorders/tumors_of_the_nervous_system/brain_tumors.html; 9 pages.
Merck Manual Colorectal Cancer accessed Aug. 21, 2014 at URL: merckmanuals.com/home/digestive_disorders/tumors_of_the_digestive_system/colorectal_cancer.html; 5 pages.
Merck Manual Breast Cancer accessed Aug. 21, 2014 at URL: merckmanuals.com/home/womens_health_issues/breast_disorders/breastcancer.html; 20 pages.
Merck Manual Prostate Cancer accessed Aug. 21, 2014 at URL: merckmanuals.com/home/kidney_and_urinary_tract_discorders/cancers_of_the_kidney_and_genitourinary_tract/prostate_cancer.html?qt=prostate cancer&alt=sh; 8 pages.
Merck Manual Ovarian Cancer accessed Aug. 21, 2014 at URL: merckmanuals.com/home/womens_health_issues/cancers_of_the_femalereproductive_system/ovarian_cancer.html?qt=ovarian cancer&alt=sh; 4 pages.
Merck Manual Bladder Cancer accessed Aug. 21, 2014 at URL: merckmanuals.com/home/kidney_and_urinary_tract_discorders/cancers_of_the_kidney_and_genitourinary_tract/bladder_cancer.html; 2 pages.
Merck Manual Cancer of the Uterus accessed Aug. 21, 2014 at URL: merckmanuals.com/home/womens_health_issues/cancers_of_the_female_reproductive_system/cancer_of_the_uterus.html?qt=Cancer of the Uterus&alt=sh; 4 pages.
Merlo et al., 5' CpG island methylation is associated with transcriptional silencing of the tumour suppressor p16/CDKN2/MTS1 in human cancers. Nat Med. (1995) 1(7): 686-692.
Mieog et al., Neoadjuvant chemotherapy for operable breast cancer. Br J Surg. Oct. 2007;94(10): 1189-1200.
Mok et al., SPARC, an extracellular matrix protein with tumor-suppressing activity in human ovarian epithelial cells. Oncogene. (1996) 12(9): 1895-1901.
Nabholtz et al., Prospective randomized trial of docetaxel versus mitomycin plus vinblastine in patients with metastatic breast cancer progressing despite previous anthracycline-containing chemotherapy. 304 Study Group. J Clin Oncol. (1999) 7(5): 1413-1424.
Napholtz et al., Phase II Study of Docetaxel, Doxorubicin, and Cyclophosphamide as First-Line Chemotherapy for Metastatic Breast Cancer. J Clin Oncol. (2001) 19: 314-321.
National Institute of Cancer: Understanding and related topics, accessed Aug. 21, 2014 at URL; cancer.gov/cancertopics/understanding cancer, 63 page.
Nyman et al., Phase I and Pharmacokinetics Trial of ABI-007, a Novel Nanoparticle Formulation of Paclitaxel in Patients with Advanced Nonhematologic Malignancies. J Clin Oncol (2005) 23(31): 7785-7793.
O'Shaughnessy et al., Weekly Nanoparticle Albumin Paclitaxel (Abraxane) Results in Long-Term Disease Control in Patients with Taxane-Refractory Metastatic Breast Cancer. 2004 SABCS. S65, Abstract No. 1070, 1 page.
Paridaens et al., Paclitaxel versus doxorubicin as first-line single-agent chemotherapy for metastatic breast cancer: a European Organization for Research and Treatment of Cancer Randomized Study with cross-over. J Clin Oncol. (2000).18(4): 724-733.
Perez et al., Overcoming Taxane Resistance in Metastatic Breast Cancer. Clin Care Options Oncology, published online at URL: clinicaloptions.com/onco in 2006; pp. 1-21, accessed Dec. 21, 2014.
Pippen, J. et al, Dose-dense doxorubicin and cyclophosphamide followed by dose-dense albumin-bound paclitaxel plus bevacizumab is safe as adjuvant therapy in patients with early stage breast cancer; Breast Cancer Res Treat. (2011) 130: 825-831.

Plagemann et al., Metabolism and cytotoxicity of 5-azacytidine in cultured Novikoff rat hepatoma and P388 mouse leukemia cells and their enhancement by preincubation with pyrazofurin. Cancer Res. (1978) 38(8): 2458-2466.
Rich et al., Gene expression profiling and genetic markers in glioblastoma survival. Cancer Res. (2005) 65(10): 4051-4058.
Robert, N. et al., Adjuvant dose-dense doxorubicin plus cyclophosphamide followed by dose-dense nab-paclitaxel is safe in women with early-stage breast cancer: a pilot study; Breast Cancer Res Treat. Jan. 2011;125(1):115-20. doi: 10.1007/s10549-010-1187-2. Epub Oct. 14, 2010.
Robertson et al., DNA methylation: past, present and future directions. Carcinogenesis. (2000) 21(3): 461-467.
Robidoux et al., Neoadjuvant chemotherapy with sequential weekly nanoparticle albumin-bound paclitaxel (ABI-007, Abraxane®) followed by 5-fluorouracil, epirubicin and cyclophosphamide (FEC) in locally advanced breast cancer (LABC): a phase II trial of the NSABP Foundation research programs (FRP) [poster]. Presented at: San Antonio Breast Cancer Symposium; Dec. 14-17, 2006; San Antonio, TX., S147, Abstract 3068; 1 page.
Robidoux, A. et al, A phase II neoadjuvant trial of sequential nanoparticle albumin-bound paclitaxel followed by 5-fluorouracil/epirubicin/cyclophosphamide in locally advanced breast cancer; Clin Breast Cancer. Feb. 2010;10(1):81-6. doi: 10.3816/CBC.2010.n.011.
Sage et al., Characterization of a novel serum albumin-binding glycoprotein secreted by endothelial cells in culture. J Biol Chem. (1984) 259(6): 3993-4007.
Sage et al., Extracellular proteins that modulate cell-matrix interactions. SPARC, Tenascin, and Thrombospondin. J Biol Chem. (1991) 266(23): 14831-14834.
Said et al., Absence of host-secreted protein acidic and rich in cysteine (SPARC) augments peritoneal ovarian carcinomatosis. Am J Pathol. (2005); 167(6): 1739-1752.
Santi et al., On the mechanism of inhibition of DNA-cytosine methyltransferases by cytosine analogs. Cell. (1983) 33: 9-10.
Sato et al., SPARC/osteonectin is a frequent target for aberrant methylation in pancreatic adenocarcinoma and a mediator of tumor-stromal interactions. Oncogene. (2003) 22(32):5021-5030.
Schultz et al., Secreted protein acidic and rich in cysteine promotes glioma invasion and delays tumor growth in vivo. Cancer Res. (2002) 62(21):6270-6277.
Semiglazov et al., Primary (neoadjuvant) chemotherapy and radiotherapy compared with primary radiotherapy alone in stage IIb-IIIa breast cancer. Ann Oncol. Sep. 1994;5(7): 591-595.
Shi et al., Targeting SPARC expression decreases glioma cellular survival and invasion associated with reduced activities of FAK and ILK kinases. Oncogene. (2007) 26(28): 4084-4094.
Silverman L.R. Targeting hypomethylation of DNA to achieve cellular differentiation in myelodysplastic syndromes (MDS). Oncologist. (2001) 6(suppl 5): 8-14.
Silverman et al., Further analysis of trials with Azacitidine in patients with myelodysplastic syndrome: studies 8421, 8921, and 9221 by the cancer and leukemia group B. J Clin Oncol. (2006) 24(24): 3895-3903.
Sjöström et al., Docetaxel compared with sequential methotrexate and 5-fluorouracil in patients with advanced breast cancer after anthracycline failure: a randomised phase III study with crossover on progression by the Scandinavian Breast Group. Eur J Cancer. (1999) 35(8): 1194-1201.
Sledge et al., Phase III trial of doxorubicin, paclitaxel, and the combination of doxorubicin and paclitaxel as front-line chemotherapy for metastatic breast cancer: An intergroup trial (E1193). J Clin Oncol. (2003) 21(4): 588-592.
Smith et al., Neoadjuvant Chemotherapy in Breast Cancer: Significantly Snhanced Sesponse with Docetaxel. J Clin Oncol. Mar. 15, 2002;20(6): 1456-1466.
Sova et al., Discovery of novel methylation biomarkers in cervical carcinoma by global demethylation and microarray analysis. Cancer Epidemiol Biomarkers Prev. (2006) 15(1): 114-123.
Sparano et al., Weekly Paclitaxel in the Adjuvant Treatment of Breast Cancer. N Eng J Med. (2008) 358(16): 1663-1671.

(56) References Cited

OTHER PUBLICATIONS

Sullivan et al., Azacitidine: a novel agent for myelodysplastic syndromes. Am J Health Syst Pharm. (2005) 62(15): 1567-1573.
Suzuki et al., Aberrant methylation of SPARC in human lung cancers. Br J Cancer. (2005) 92(5): 942-948.
Tai et al., Genome-wide expression analysis of therapy-resistant tumors reveals SPARC as a novel target for cancer therapy. J Clin Invest. (2005) 115(6): 1492-1502.
Tremble et al. SPARC, a secreted protein associated with morphogenesis and tissue remodeling, induces expression of metalloproteinases in fibroblasts through a novel extracellular matrix-dependent pathway. J Cell Biol. (1993) 121(6): 1433-1444.
Uchida et al., Hypermethylation of the p15INK4B gene in myelodysplastic syndromes. Blood. (1997) 90(4): 1403-1409.
Ueno et al., 5-Azacytidine (5AzC)-induced histopathological changes in the central nervous system of rat fetuses. Exp Toxic Pathol. (2002) 54:91-96.
Van der Hage et al., Preoperative chemotherapy in primary operable breast cancer: results from the European Organization for Research and Treatment of Cancer trial 10902. J Clin Oncol. Nov. 15, 2001;19(22): 4224-4237.
Van der Velden et al., Promoter hypermethylation: A common cause of reduced p16INK4a expression in uveal melanoma. Cancer Res. (2001) 61(13): 5303-5306.
Vernon et al., Adhesion, shape, proliferation, and gene expression of mouse Leydig cells are influenced by extracellular matrix in vitro. Biol Reprod. (1991) 44(1): 157-170.
Von Hoff et al., 5-Azacytidine. A new anticancer drug with effectiveness in acute myelogenous leukemia. Ann Intern Med. (1976) 85(2): 237-245.
Von Minckwitz et al., In vivo chemosensitivity-adapted preoperative chemotherapy in patients with early-stage breast cancer: the GEPARTRIO pilot study. Ann Oncol. Jan. 2005;16(1): 56-63.
Von Minckwitz et al., Comparison of neoadjuvant 6 vs 8 cycles of docetaxel/doxorubicin/cyclophosphamide (TAC) in patients early responding to TACx2—the GEPARTRIO Study. Journal of Clinical Oncology, 2006 ASCO Annual Meeting Proceedings (Post-Meeting Edition). No. 18S (Jun. 20 Supplement), 2006: 576 [Abstract Only].
Watkins et al., Increased levels of SPARC (osteonectin) in human breast cancer tissues and its association with clinical outcomes. Prostaglandins Leukot Essent Fatty Acids. (2005) 72(4): 267-272.
Wolmark et al., Preoperative chemotherapy in patients with operable breast cancer: nine-year results from National Surgical Adjuvant Breast and Bowel Project B-18. J Natl Cancer Inst Monogr. 2001;(30): 96-102.
Yang et al., Frequent inactivation of SPARC by promoter hypermethylation in colon cancers. Int J Cancer. (2007) 121(3): 567-575.
Yardley et al., A pilot study of adjuvant anoparticle albumin-bound (nab) paclitaxel and cyclophosphamide, with trastuzumab in HER2-positive patients, in the t4reatment of early-stage breast cancer. Breast Cancer Res Treat. (Jul. 2010) 123: 471-475.
Yiu et al., SPARC (secreted protein acidic and rich in cysteine) induces apoptosis in ovarian cancer cells. Am J Pathol. (2001) 159(2): 609-622.
International Search Report dated Aug. 7, 2012 received in International Application No. PCT/US2012/023530.
International Search Report dated Nov. 16, 2012 received in International Application No. PCT/US2012/038111.
Office Action in U.S. Appl. No. 13/982,743 dated Aug. 27, 2014.
Response to Office Action in U.S. Appl. No. 13/982,743, filed Jan. 26, 2015.
Office Action in U.S. Appl. No. 13/982,743 dated Feb. 20, 2015.
Response to Office Action in U.S. Appl. No. 13/982,743, filed May 19, 2015.
Office Action in U.S. Appl. No. 13/982743 dated Aug. 24, 2015.
Response to Office Action in U.S. Appl. No. 13/982,743, filed Nov. 20, 2015.
Office Action in U.S. Appl. No. 13/982,743 dated Feb. 25, 2016.

COMBINATION THERAPY FOR TREATMENT OF CANCER

RELATED APPLICATIONS

This application, is a continuation of U.S. Ser. No. 14/117,832 filed Nov. 14, 2013 entitled "COMBINATION THERAPY FOR TREATMENT OF CANCER" which is the U.S. National Phase of PCT Application No. PCT/US2012/038111 entitled "COMBINATION THERAPY FOR TREATMENT OF CANCER" filed May 16, 2012, and published in English on Nov. 22, 2012 as WO 2012/158776 which claims the benefit of U.S. Provisional Application No. 61/487,232 entitled "COMBINATION THERAPY FOR TREATMENT OF CANCER" filed May 17, 2011, the disclosure of which is incorporated herein by reference in its entirety.

FIELD OF THE INVENTION

The present invention relates to methods and compositions for the treatment of cancer. Some embodiments include methods of treating cancer comprising administering a chemotherapeutic agent associated with or bound to albumin, administering a second chemotherapeutic agent; and administering a third chemotherapeutic agent.

BACKGROUND OF THE INVENTION

Breast cancer is the most common cancer among women (excluding basal and squamous cell skin cancer) in the U.S. and is the second most common cause of cancer death among women. In the year 2007, the estimated new cases of breast cancer among women in the U.S. is 178,480 and the estimated death from breast cancer is 40,460 (1).

Neoadjuvant chemotherapy for breast cancer is the use of chemotherapy before definitive surgical therapy such as lumpectomy or mastectomy. Compared with adjuvant or postoperative chemotherapy, neoadjuvant chemotherapy allows higher rates of breast conservation without compromising overall survival (2). In addition, neoadjuvant chemotherapy permits a unique opportunity to observe and evaluate tumor response to treatment and therefore, serving as an in vivo chemosensitivity assay. This may allow the tailoring of treatment for individual patients based on their tumor response to a particular chemotherapy regimen (3-5). This may potentially enhance response and survival and at the same time reduce unnecessary toxicities.

Not only neoadjuvant chemotherapy does result in similar overall survival compared with adjuvant chemotherapy, it is also associated with less adverse toxicities (6). Compared with adjuvant chemotherapy, neoadjuvant chemotherapy is associated with significantly less infectious complications and cardiotoxicity (6). In addition, there is suggestive evidence that neoadjuvant chemotherapy may be superior to adjuvant chemotherapy on survival outcome (7). In contrast with adjuvant chemotherapy, there is currently no clear recommendation on neoadjuvant chemotherapy regimens. There is a need for improved therapies for cancer.

SUMMARY OF THE INVENTION

Some embodiments of the present invention include methods of treating a cancer in a subject in need thereof comprising administering a chemotherapeutic agent associated with or bound to albumin; administering a second chemotherapeutic agent; and administering a third chemotherapeutic agent.

In some embodiments, the chemotherapeutic agent associated with or bound to albumin is administered periodically.

In some embodiments, the chemotherapeutic agent associated with or bound to albumin the second chemotherapeutic agent and a third chemotherapeutic agent are administered on the same day and subsequently the chemotherapeutic agent associated with or bound to albumin is administered, periodically without the second chemotherapeutic agent and the third chemotherapeutic agent.

In some embodiments, on some occasions the chemotherapeutic agent associated with or bound to albumin the second chemotherapeutic agent and a third chemotherapeutic agent are administered on the same day and on other occasions only the chemotherapeutic agent associated with or bound to albumin is administered.

In some embodiments, the chemotherapeutic agent associated with or bound to albumin comprises an agent selected from the group consisting of paclitaxel, docetaxel, and rapamycin.

In some embodiments, the chemotherapeutic agent associated with or bound to albumin is nab-paclitaxel (ABRAXANE®).

In some embodiments, the second chemotherapeutic agent comprises a topoisomerase inhibitor.

In some embodiments, the topoisomerase inhibitor is doxorubicin.

In some embodiments, the third chemotherapeutic agent comprises an alkylating agent.

In some embodiments, the alkylating agent is cyclophosphamide.

In some embodiments, the chemotherapeutic agent associated with or bound to albumin is administered on days 1 and 8.

In some embodiments, the chemotherapeutic agent associated with or bound to albumin is administered on days 1, 8, 15.

In some embodiments, the chemotherapeutic agent associated with or bound to albumin is administered on days 1, 8, 15, and 22.

In some embodiments, the chemotherapeutic agent associated with or bound to albumin is administered on days 1, 8, 15, 22, and 28.

In some embodiments, the chemotherapeutic agent associated with or bound to albumin is administered on days 1, 8, and 22.

In some embodiments, the chemotherapeutic agent associated with or bound to albumin is administered at an interval of at least about 5 days.

In some embodiments, the chemotherapeutic agent associated with or bound to albumin is administered at an interval of at least about 6 days.

In some embodiments, the chemotherapeutic agent associated with or bound to albumin is administered at an interval of at least about 7 days.

In some embodiments, the periodic administration comprises at least 2 cycles.

In some embodiments, the periodic administration comprises at least 5 cycles.

In some embodiments, the chemotherapeutic agent associated with or bound to albumin the second chemotherapeutic agent and the third chemotherapeutic agent are administered, on the same day and subsequently the administration of the chemotherapeutic agent associated with or bound to albumin is repeated for a plurality of cycles.

In some embodiments, the plurality of cycles for the subsequent administration of the chemotherapeutic agent associated with or bound to albumin comprises at least 2 cycles.

In some embodiments, the plurality of cycles for the subsequent administration of the chemotherapeutic agent associated with or bound to albumin comprises at least 5 cycles.

In some embodiments, each cycle for the subsequent administration of the chemotherapeutic agent associated with or bound to albumin comprises at least about 5 days.

In some embodiments, each cycle for the subsequent administration of the chemotherapeutic agent associated with or bound to albumin comprises at least about 6 days.

In some embodiments, each cycle for the subsequent administration of the chemotherapeutic agent associated with or bound to albumin comprises at least about 7 days.

In some embodiments, each cycle for the subsequent administration of the chemotherapeutic agent associated with or bound to albumin comprises at least about 1 week.

In some embodiments, at least about 100 mg/m$^2$ nab-paclitaxel (ABRAXANE®) is administered on day 1 and 8, at least about 50 mg/m$^2$ doxorubicin is administered on day 1, and at least about 500 mg/m$^2$ cyclophosphamide is administered on day 1.

Some embodiments also include administering Pegfilgrastim on day 9.

In some embodiments, the cancer is breast cancer.

In some embodiments, the cancer is HER2 negative breast cancer.

In some embodiments, the cancer is triple negative breast cancer.

In some embodiments, the dose of nab-paclitaxel (ABRAXANE®) is between about 50 mg/m$^2$ and about 200 mg/m$^2$.

In some embodiments, the dose of nab-paclitaxel (ABRAXANE®) is selected from the group consisting of 100 mg/m$^2$ and 150 mg/m2.

Some embodiments include use of a combination comprising a chemotherapeutic agent associated with or bound to albumin, a second chemotherapeutic agent, and a third chemotherapeutic agent for the treatment of cancer.

In some embodiments, the chemotherapeutic agent associated with or bound to albumin is administered periodically.

In some embodiments, the chemotherapeutic agent associated with or bound to albumin the second chemotherapeutic agent and a third chemotherapeutic agent are administered on the same day and subsequently the chemotherapeutic agent associated with or bound to albumin is administered periodically without the second chemotherapeutic agent and the third chemotherapeutic agent.

In some embodiments, on some occasions the chemotherapeutic agent associated with or bound to albumin the second chemotherapeutic agent and a third chemotherapeutic agent are administered on the same day and on other occasions only the chemotherapeutic agent associated with or bound to albumin is administered.

In some embodiments, the chemotherapeutic agent associated with or bound to albumin comprises an agent selected from the group consisting of paclitaxel, docetaxel, and rapamycin.

In some embodiments, the chemotherapeutic agent associated with or bound to albumin is nab-paclitaxel (ABRAXANE®).

In some embodiments, the second chemotherapeutic agent comprises a topoisomerase inhibitor.

In some embodiments, the topoisomerase inhibitor is doxorubicin.

In some embodiments, the third chemotherapeutic agent comprises an alkylating agent.

In some embodiments, the alkylating agent is cyclophosphamide.

In some embodiments, the chemotherapeutic agent associated with or bound to albumin is administered on days 1 and 8.

In some embodiments, the chemotherapeutic agent associated with or bound to albumin is administered on days 1, 8, 15.

In some embodiments, the chemotherapeutic agent associated with or bound to albumin is administered on days 1, 8, 15, and 22.

In some embodiments, the chemotherapeutic agent associated with or bound to albumin is administered on days 1, 8, 15, 22, and 28.

In some embodiments, the chemotherapeutic agent associated with or bound to albumin is administered on days 1, 8, and 22.

In some embodiments, the chemotherapeutic agent associated with or bound to albumin is administered at an interval of at least about 5 days.

In some embodiments, the chemotherapeutic agent associated with or bound to albumin is administered at an interval of at least about 6 days.

In some embodiments, the chemotherapeutic agent associated with or bound to albumin is administered at an interval of at least about 7 days.

In some embodiments, the periodic administration comprises at least 2 cycles.

In some embodiments, the periodic administration comprises at least 5 cycles.

In some embodiments, the chemotherapeutic agent associated with or bound to albumin the second chemotherapeutic agent and the third chemotherapeutic agent are administered on the same day and subsequently the administration of the chemotherapeutic agent associated with or bound to albumin is repeated for a plurality of cycles.

In some embodiments, the plurality of cycles for the subsequent administration of the chemotherapeutic agent associated with or bound to albumin comprises at least 2 cycles.

In some embodiments, the plurality of cycles for the subsequent administration of the chemotherapeutic agent associated with or bound to albumin comprises at least 5 cycles.

In some embodiments, each cycle for the subsequent administration of the chemotherapeutic agent associated with or bound, to albumin comprises at least about 5 days.

In some embodiments, each cycle for the subsequent administration of the chemotherapeutic agent associated with or bound to albumin comprises at least about 6 days.

In some embodiments, each cycle for the subsequent administration of the chemotherapeutic agent associated with or bound to albumin comprises at least about 7 days.

In some embodiments, each cycle for the subsequent administration of the chemotherapeutic agent associated with or bound to albumin comprises at least about 1 week.

In some embodiments, at least about 100 mg/m$^2$ nab-paclitaxel (ABRAXANE®) is administered on day 1 and 8, at least about 50 mg/m$^2$ doxorubicin is administered, on day 1, and at least about 500 mg/m$^2$ cyclophosphamide is administered on day 1.

Some embodiments also include administering Pegfilgrastim on day 9.

In some embodiments, the cancer is breast cancer.

In some embodiments, the cancer is HER2 negative breast cancer.

In some embodiments, the cancer is triple negative breast cancer.

In some embodiments, the dose of nab-paclitaxel (ABRAXANE®) is between about 50 mg/m$^2$ and about 200 mg/m$^2$.

In some embodiments, the dose of nab-paclitaxel (ABRAXANE®) is selected from the group consisting of 100 mg/m$^2$ and 150 mg/m$^2$.

DETAILED DESCRIPTION

The present invention relates to methods and compositions for the treatment of cancer. Some embodiments include methods of treating cancer comprising administering a chemotherapeutic agent associated with or bound to albumin, administering a second chemotherapeutic agent; and administering a third chemotherapeutic agent.

Currently, there is no cure for patients with metastatic breast cancer. Therefore, treating patients with early stage breast cancer, either before surgery (neoadjuvant) or after surgery (adjuvant) is an important strategy to reduce the chance of cancer recurrence locally or distally, thereby reducing morbidity and mortality.

Triple-negative breast cancer includes breast cancers that do not express the genes for estrogen receptor (ER), progesterone receptor (PR) or Her2/neu. This subtype of breast cancer is clinically characterized as more aggressive and, less responsive to standard treatment and associated poorer overall patient prognosis. Basal-like or triple negative breast cancer cells express high levels of Secreted protein, acidic, cysteine-rich (SPARC) protein, also known as osteonectin, which binds and entraps albumin. Overexpression of SPARC protein has also been reported in many human cancers such as, prostate and colon cancers.

Expression of SPARC protein by cancer cells can be useful to target chemotherapeutic agents to a tumor. In an example pathway, activation of a specific receptor (gp60) on the endothelial cell wall in turn activates the protein, caveolin-1. Caveolin-1 can initiate the formation of caveolae which can transport materials, such as chemotherapeutic agents associated with albumin to the tumor interstitium (17). SPARC protein expressed by the tumor may bind and entrap the chemotherapeutic agents associated with or bound to albumin (18). Nab-paclitaxel (ABRAXANE®) is an example of a chemotherapeutic agent associated with albumin.

There is currently no clear recommendation on neoadjuvant chemotherapy regimens. Doxorubicin (Adriamycin) and taxanes are active drugs against breast cancer. A regimen of Taxotere, Adriamycin, and Cyclophosphamide (TAC) administered every three weeks for 6 cycles, is among the most active regimens in the adjuvant and neoadjuvant settings (3, 13, 14). However, the pathologic complete response rate, which is a surrogate for long term survival, is quite low for this regimen. A regimen of nab-paclitaxel (ABRAXANE®) administered weekly can provide an increased positive response in patients with lower side effects, compared to a regimen of administering Taxotere every 3 weeks. Some methods described herein include regimens including administration of Nab-paclitaxel, Adriamycin, and Cytoxan (NAC).

The TAC regimen (docetaxel, doxorubicin, and cyclophosphamide) is among the most active drug combinations in the adjuvant and neoadjuvant settings. A weekly nab-paclitaxel is superior to every-three week docetaxel in both efficacy and toxicity in patients with metastatic breast cancer. Provided herein are results of a single center phase I study in which nab-paclitaxel replaces docetaxel in the conventional TAC regimen.

Albumin-Associated or Albumin-Bound Chemotherapeutic Agents

Some embodiments of the methods and compositions described herein include chemotherapeutic agents associated with or bound to albumin. Examples of chemotherapeutic agents which may be associated with or bound to albumin include Vinca alkaloids (e.g., Vinblastine, Vincristine, Vinflunine, Vindesine, Vinorelbine) Taxanes (e.g., Cabazitaxel, Docetaxel, Larotaxel, Ortataxel, Paclitaxel, Tesetaxel) and Epothilones (e.g., Ixabepilone), dihydrofolate reductase inhibitors (e.g., Aminopterin, Methotrexate, Pemetrexed, Pralatrexate), thymidylate synthase inhibitors (e.g., Raltitrexed, Pemetrexed), adenosine deaminase inhibitors (e.g., Pentostatin), ribonucleotide reductase inhibitors (e.g., Cladribine, Clofarabine, Fludarabine), thiopurine (e.g., Thioguanine, Mercaptopurine), thymidylate synthase inhibitors (e.g., Fluorouracil, Capecitabine, Tegafur, Carmofur, Floxuridine), DNA polymerase inhibitors (e.g., Cytarabine), ribonucleotide reductase inhibitors (e.g., Gemcitabine), hypomethylating agents (e.g., Azacitidine, Decitabine), ribonucleotide reductase inhibitors (e.g., Hydroxycarbamide), Topoisomerase inhibitors (e.g., Camptothecin, Topotecan, Irinotecan, Rubitecan, Belotecan, Etoposide, Teniposide, Anthracyclines such as Aclarubicin, Daunorubicin, Doxorubicin, Epirubicin, Idarubicin, Amrubicin, Pirarubicin, Valrubicin, Zorubicin, and Anthracenediones such as Mitoxantrone, Pixantrone), Alkylating agents (e.g., Mechlorethamine, Cyclophosphamide such as Ifosfamide and Trofosfamide, Chlorambucil such as Melphalan, Prednimustine, as well as Bendamustine, Uramustine, Nitrosoureas such as Carmustine, Lomustine, Fotemustine, Nimustine. Ranimustine. Streptozocin, Alkyl sulfonates such as Busulfan, Mannosulfan, and Treosulfan, and Aziridines such as Carboquone, ThioTEPA, Triaziquone, and Triethylenemelamine), Platinums (e.g., Carboplatin, Cisplatin, Nedaplatin, Oxaliplatin, Triplatin tetranitrate, and Satraplatin), Hydrazines (e.g., Procarbazine), Triazenes (e.g., Dacarbazine, Temozolomide), Altretamine, and Mitobronitol, Intercalation agents (e.g., Actinomycin, Bleomycin, Mitomycin, Plicamycin). More examples of chemotherapeutic agents include Aminolevulinic acid, Efaproxiral, Porphyrin derivatives (e.g., Porfimer sodium, Talaporfin, Temoporfin, Verteporfin), Enzyme inhibitors (e.g., Tipifarnib, Alvocidib, Seliciclib, Bortezomib, Anagrelide, Tiazofurine, Masoprocol, Olaparib, Vorinostat, Romidepsin), Atrasentan, Bexarotene, Testolactone, Amsacrine, Trabectedin, Alitretinoin, Tretinoin, Arsenic trioxide, Celecoxib, Demecolcine, Elesclomol, Elsamitrucin, Etoglucid, Lonidamine, Lucanthone, Mitoguazone, Mitotane, Oblimersen, Omacetaxine mepesuccinate, Everolimus, and Temsirolimus.

In some embodiments, the chemotherapeutic agent and albumin comprise a nanoparticle. Examples nanoparticle include nab-paclitaxel (ABRAXANE®). Nab-paclitaxel (ABRAXANE®) is a novel biologically interactive albumin-bound paclitaxel combining a protein with a chemotherapeutic agent in the particle form. Nab-paclitaxel (ABRAXANE®) is an example of an interactive nanoparticle leveraging this gp-60/caveolin-1/caveolae/SPARC pathway to increase intra-tumoral concentration of the drug and reducing toxic drug in normal tissue.

In some embodiments of the methods and uses provided herein, two or more of the chemotherapeutic agents described herein can be administered to a subject in need thereof. In some embodiments, three or more of the chemotherapeutic agents described herein can be administered to a subject in need thereof. In some such embodiments, at least one of the chemotherapeutic agents administered to the subject comprises a chemotherapeutic agent associated with or bound to albumin.

Preclinical and Clinical Studies with Nab-Paclitaxel (ABRAXANE®)

Preclinical studies comparing nab-paclitaxel (ABRAXANE®) to Taxol demonstrated, lower toxicities, with a maximum tolerated dose (MTD) approximately 50% higher for nab-paclitaxel (ABRAXANE®) compared to Taxol. At equal doses there was less myelosuppression and improved efficacy in a xenograft tumor model of human mammary adenocarcinoma. At equitoxic doses of paclitaxel, nab-paclitaxel (ABRAXANE®) was found to be markedly more efficacious than Taxol (19).

Every 3 Weeks Schedule

In a phase I study, the MTD of nab-paclitaxel (ABRAXANE®) was determined to be 300 mg/m$^2$ by 30 minute infusion every 3 weeks, without premedication or G-CSF support (20). No severe hypersensitivity reactions occurred with nab-paclitaxel (ABRAXANE®) despite the absence of premedication. Dose-limiting toxicities included sensory neuropathy, stomatitis, and superficial keratopathy, which occurred at a dose of 375 mg/m$^2$.

Two multicenter phase II studies have evaluated 2 dose levels of nab-paclitaxel (ABRAXANE®) (300 mg/m$^2$, n=63, and 175 mg/m$^2$, n=43) in patients with metastatic breast cancer (21, 22). The overall response rates in these 2 phase II trials were 40% (95% CI 25-54%) for the 175 mg/m$^2$ dose, and 48% (95% CI 35-60%) for the 300 mg/m$^2$ dose. Of 39 patients receiving 300 mg/m$^2$ as first-line therapy for metastatic breast cancer, 64% (95% CI 49-79%) responded. This was contrasted with a 45% response rate in similar patients at the lower dose level. Grade 4 neutropenia was noted in 24% of patients at the higher dose level, occurred primarily during the first cycle and resolved rapidly.

A Phase III trial in patients with metastatic breast cancer compared nab-paclitaxel (ABRAXANE®) 260 mg/m$^2$ to Taxol 175 mg/m$^2$ given every 3 weeks (23). Efficacy analyses were based on the intent-to-treat (ITT) population. The overall response rate (ORR) was significantly greater for nab-paclitaxel (ABRAXANE®) than for Taxol for all patients (33% v 19%, respectively; P=0.001), patients who received first-line therapy (42% v 27%, respectively; P=0.029), patients who received second-line or greater therapy (27% v 13%, respectively; P=0.006), and patients who had received prior anthracycline therapy in either the adjuvant/metastatic setting (34% v 18%, respectively; P=0.002) or the metastatic setting only (27% v 14%, respectively; P=0.010). Tumor response rate was also significantly higher for nab-paclitaxel (ABRAXANE®) than for Taxol in patients with visceral dominant lesions (34% v 19%, respectively; P=0.002) and in patients aged younger than 65 years (34% v 19%, respectively; P<0.001). ORR also was greater for nab-paclitaxel (ABRAXANE®) compared with standard paclitaxel in patients with nonvisceral dominant lesions (34% v 19%, respectively) and in patients ≥65 years old (27% v 19%, respectively), but the results did not reach statistical significance because of the small number of patients in these subsets.

Median time to tumor progression (TTP) was significantly longer with nab-paclitaxel (ABRAXANE®) than with Taxol for all patients (23.0 v 16.9 weeks, respectively; hazard ratio [HR]=0.75; P=0.006). There was a trend, for greater median survival for all patients treated with nab-paclitaxel (ABRAXANE®) than with Taxol (65.0 v 55.7 weeks, respectively; P=0.374). Although no difference in survival was observed in first-line patients, the difference was statistically significant in patients who received nab-paclitaxel (ABRAXANE®), compared with Taxol, as second-line or greater therapy (56.4 v 46.7 weeks, respectively; HR=0.73; P=.024) (23).

The incidence of hypersensitivity reactions (any grade) was low for both arms (1% for nab-paclitaxel (ABRAXANE®) and 2% for Taxol). No severe (grade 3 or 4) treatment-related hypersensitivity reactions occurred in any of the patients in the nab-paclitaxel (ABRAXANE®) group despite the absence of premedication. In contrast, grade 3 hypersensitivity reactions occurred in the Taxol group despite standard premedication (chest pain, two patients; allergic reaction, three patients). Per protocol, corticosteroids and antihistamines were not administered routinely to patients in the nab-paclitaxel (ABRAXANE®) group; however, premedication was administered for emesis, myalgia/arthralgia, or anorexia in 18 patients (8%) in the nab-paclitaxel (ABRAXANE®) group in 2% of the treatment cycles, whereas 224 patients (>99%) in the Taxol group received premedication in 95% of the cycles.

Although the patients in the nab-paclitaxel (ABRAXANE®) group received an average paclitaxel dose-intensity 49% greater than that received by patients in the Taxol group, the incidence of treatment-related grade 4 neutropenia was significantly lower in the nab-paclitaxel (ABRAXANE®) group than in the Taxol group (9% v 22%, respectively; P<0.001), with a higher mean neutrophil nadir (1.67 v 1.31×10$^9$/L, respectively; P=0.046), suggesting that polyethylated castor oil may have contributed to this toxicity in patients who received standard paclitaxel.

As expected with a higher dose of paclitaxel, treatment-related grade 3 sensory neuropathy occurred more frequently in the nab-paclitaxel (ABRAXANE®) arm than in the Taxol arm (10% v 2%, respectively; P<0.001); however, these episodes improved with interruption, of treatment to grade 2 or 1 in a median 22 days and were easily managed with treatment interruption and dose reduction. By day 28 after its first occurrence, the number of patients with persistent grade 3 sensory neuropathy was the same (n=4) in both study arms. No episodes of motor neuropathy or grade 4 sensory neuropathy were reported in either group.

The only clinical chemistry value that was notably different between the two treatment arms was higher serum glucose levels in the Taxol—treated patients, who also had a higher incidence of hyperglycemia reported as an adverse effect (AE) compared with nab-paclitaxel (ABRAXANE®)—treated patients (7% v 1% respectively; P=0.003).

Subgroup analyses revealed that the safety profiles of nab-paclitaxel (ABRAXANE®) and Taxol in patients who received the drugs as first-line therapy were similar to those in the overall study population. In subgroup analyses by age, the reported AEs were similar in patients less than 65 years old and patients ≥65 years old in both groups. Of the patients ≥65 years old, the incidences of the following AEs were notably lower in the nab-paclitaxel (ABRAXANE®) group than in the Taxol group: neutropenia (23% v 59%, respectively), leukopenia (10% v 31%, respectively), nausea (20% v 38%, respectively), hyperglycemia (0% v 19%, respectively), and flushing (0% v 16%, respectively). These data indicate no additional safety concerns for nab-paclitaxel (ABRAXANE®) in patients ≥65 years old compared with younger patients.

Six patients (3%) in the nab-paclitaxel (ABRAXANE®) group and eight patients (4%) in the standard paclitaxel group died during the study, all as a result of disease progression. No treatment-related deaths occurred in the nab-paclitaxel (ABRAXANE®) group; one patient (<1%) in the Taxol group died of multiorgan failure, which was considered by the investigator to be possibly related to treatment but may also have been a result of sepsis and/or progressive disease.

Weekly for 3 Weeks, Every 4 Weeks Schedule

Thirty-nine patients were enrolled into A Phase I study of nab-paclitaxel (ABRAXANE®) administered weekly for 3 weeks followed by a 1 week rest in patients with advanced solid tumors (24). The MTDs for heavily and lightly pretreated patients were 100 and 150 mg/m2 respectively. Dose limiting toxicities included grade 4 neutropenia and grade 3 sensory neuropathy. Premedication was not required, and unexpected, non-taxane associated toxicities were not observed.

In a Phase II trial in heavily pretreated patients with taxane-refractory metastatic breast cancer, objective antitumor responses occurred in 15% of women treated with nab-paclitaxel (ABRAXANE®) 100 mg/m2 on this schedule (25). Nab-paclitaxel (ABRAXANE®) weekly regimen was well tolerated. 91% of patients were treated at the full dose of 100 mg/m2 of nab-paclitaxel (ABRAXANE®) without dose reductions. Based on the activity and low toxicity documented with the nab-paclitaxel (ABRAXANE®) 100 mg/m2 weekly regimen, this study was expanded to evaluate the efficacy and safety/tolerability of a higher dose of nab-paclitaxel (ABRAXANE®) 125 mg/m$^2$ weekly regimen in 75 additional patients. Results of this dose-finding study confirm the dose of nab-paclitaxel (ABRAXANE®) 100 mg/m$^2$ as the appropriate dose for further study in this patient population (26).

Weekly Schedule

The NSABP studied the administration of nab-paclitaxel (ABRAXANE®) in a neoadjuvant setting to patients with locally advanced breast cancer at a dose of 100 mg/m$^2$ weekly for 12 weeks, with no break (27). Four cycles of FEC were administered sequentially based on patients' HER2 status: HER2 negative patients received FEC-100 (F: 500 mg/m$^2$, E: 100 mg/m$^2$, C: 500 mg/m$^2$ Q3 weeks) and HER2 positive patients received weekly trastuzumab in addition to FEC-75 (F: 500 mg/m$^2$, E: 75 mg/m$^2$, C: 500 mg/m$^2$ Q3 weeks). Weekly trastuzumab was permitted during nab-paclitaxel (ABRAXANE®) and FEC-75 treatment at the discretion of the investigator. The primary objective of the trial was to determine the pathologic complete response rate (pCR) in the breast. At the time of initial report at SABCS 2006, 65 patients had been entered on study and were evaluable for cCR and safety. Following 12 weeks of nab-paclitaxel (ABRAXANE®), a clinical complete response rate (cCR) of 32% was noted. The therapy was well tolerated, with 48/65 patients receiving 12 doses in 12 weeks and 13/65 receiving 12 doses in 13-14 weeks. The incidence of peripheral (sensory) neuropathy was low (11% grade 2 and 5% grade 3) as was neutropenia (3% grade 3 and no grade 4). The authors concluded that the administration of nab-paclitaxel (ABRAXANE®) 100 mg/m$^2$ weekly×12 was both effective and tolerable.

A recent phase II study has also demonstrated that weekly nab-paclitaxel (ABRAXANE®) is superior to every-three week Taxotere in both efficacy and toxicity profile, in the treatment of patients with advanced or metastatic breast cancer (28). The rate of grade 4 neutropenia was 75% in the Taxotere group, compared to only 5% of the weekly nab-paclitaxel (ABRAXANE®) groups. Therefore, the use of growth factor support such as Neulasta that is often employed upfront in the TAC regimen (Taxotere, Adriamycin, Cyclophosphamide) may be omitted or reduced when Taxotere is replaced by nab-paclitaxel (ABRAXANE®). This may also help reduce the toxicity and overall cost of treatments (Neulasta is an expensive drug and adds considerably to the cost of treatments).

Commercial Chemotherapy

Doxorubicin and cyclophosphamide are commercially available drugs that are commonly used, in the treatment of breast cancer. See e.g., the *Physicians' Desk Reference*, incorporated herein by reference, in its entirety.

Method for Treating Cancer

Some embodiments include methods of treating a cancer in a subject in need thereof. In some embodiments, the cancer is breast cancer. In some embodiments, the cancer is HER2 negative breast cancer. In some embodiments, the cancer is triple negative breast cancer. Some such methods include administering a chemotherapeutic agent associated with or bound to albumin, administering a second chemotherapeutic agent; and administering a third chemotherapeutic agent. In some embodiments, the chemotherapeutic agent associated with or bound to albumin is administered periodically. In some embodiments, the chemotherapeutic agent associated with or bound to albumin comprises an agent selected from the group consisting of paclitaxel, docetaxel, and rapamycin. In particular embodiments, the chemotherapeutic agent associated with or bound to albumin is nab-paclitaxel (ABRAXANE®).

In some embodiments, the second chemotherapeutic agent comprises a topoisomerase inhibitor. Examples of topoisomerase inhibitors are described herein and can include doxorubicin. In some embodiments, the third chemotherapeutic agent comprises an alkylating agent. Examples of alkylating agents are described herein and can include cyclophosphamide.

In some embodiments, the chemotherapeutic agent associated with or bound to albumin is administered on days 1 and 8, or on, days 1, 8, 15, or on days 1, 8, 15, and 22, or on days 1, 8, 15, 22, and 28, or on days 1, 8, and 22. In some embodiments, the chemotherapeutic agent associated with or bound to albumin is administered at an interval of at least about 2 days, at least about 3 days, at least about 4 days, at least about 5 days, at least about 6 days, at least about 7 days, at least about 8 days, at least about 9 days, and at least about 10 days. In some embodiments, the administration of the chemotherapeutic agent associated with or bound to albumin; the administration of the second chemotherapeutic agent; and/or the administration of the third chemotherapeutic agent are repeated for a plurality of cycles. In some embodiments, the plurality of cycles is at least 2, 3, 4, 5, 6, 7, 8, 9, or 10 cycles.

In some embodiments, the dose of a chemotherapeutic agent associated with or bound to albumin, such as nab-paclitaxel (ABRAXANE®), is between about 50 mg/m$^2$ and about 200 mg/m$^2$. In some embodiments, the dose of a chemotherapeutic agent associated with or bound to albumin, such as nab-paclitaxel (ABRAXANE®), is selected from the group consisting of about 100 mg/m$^2$ and about 150 mg/m$^2$.

In some embodiments, at least about 100 mg/m$^2$ nab-paclitaxel (ABRAXANE®) is administered on day 1 and 8, at least about 50 mg/m$^2$ doxorubicin is administered on day 1, and at least about 500 mg/m$^2$ cyclophosphamide is administered on day 1. Some such embodiments also include, administering Pegfilgrastim. In some embodiments, Pegfilgrastim is administered on day 9.

EXAMPLES

Example 1—Phase I Study of Neoadjuvant Chemotherapy with Nanoparticle Albumin Bound Paclitaxel, Doxorubicin and Cyclophosphamide A Phase I study of neoadjuvant chemotherapy with nanoparticle albumin bound paclitaxel, doxorubicin, and cyclophosphamide (NAC) in patients with stages II-III HER-2 negative breast, cancer was carried out.

Background: The TAC regimen (docetaxel, doxorubicin, and cyclophosphamide) is among the most active drug combinations in the adjuvant and neoadjuvant settings. A weekly nab-paclitaxel is superior to every-three week docetaxel in both efficacy and toxicity in patients with metastatic breast cancer. Provided herein are results of a single center phase I study in which nab-paclitaxel replaces docetaxel in the conventional TAC regimen.

Methods: Women with HER-2 negative stages II-III breast cancer were enrolled. Eligible patients received 6 cycles of the NAC regimen: nab-paclitaxel (100-150 mg/m$^2$, days 1 and 8), doxorubicin (50 mg/m$^2$, day 1), and cyclophosphamide (500 mg/m$^2$, day 1). Peg-filgrastim was given on day 9. Table 1 shows nab-paclitaxel (ABRAXANE®) dose schedules.

TABLE 1

| Dose level | nab-paclitaxel (ABRAXANE ®) dose (mg/m$^2$) | Dose schedule (days) |
|---|---|---|
| −1 | 100 | 1, 8, rest |
| 0 | 100 | 1, 8, 15, 22, 29, rest |
| 1 | 150 | 1, 8, rest, 22, 29, rest |
| 2 | 150 | 1, 8, 15, 22, 29, rest |

Results: Sixteen patients enrolled in the study, one of which was a screen failure. Median tumor size was 6 cm. Median age was 54 years (40-69). ER+ tumors accounted for 53%, and 47% were triple negative. There were two inflammatory breast cancers. After the first three patients on dose level 0 (nab-paclitaxel of 100 mg/m$^2$, weekly 5 on 1 off, Q 6 weeks) experienced several dose delays because of grades 3 and 4 neutropenia, the protocol was amended such that dose level −1 (nab-paclitaxel of 100 mg/m$^2$, weekly 2 on 1 off, Q 3 weeks) would be the new starting point and there would be no further dose escalation. There was no dose limiting toxicity (DLT). To date, a total of 57 cycles of dose level −1 were given. 43.8% required dose delay. There were two episodes of febrile neutropenia. The pathologic complete response (pCR) by physical examination was 93.3%. One patient had a minimal response. The median number of cycles required before a pCR was 2. Even though pCR was not a primary end point, we observed a very favorable pCR rate. Eight patients already underwent surgery. The pCR rate for this group was 50%. Another patient had a near pCR, with microscopic residual disease. The pCR for the 4 triple negative patients was 100%.

Conclusions: This single center phase I study demonstrated safety and dramatic activity for the neoadjuvant NAC regimen in patients with stages II-III HER-2 negative breast cancer. This regimen was highly effective with impressive clinical and pathologic complete responses.

Example 2—Determination of Dosage Regimens

Other dosage regimens for chemotherapy with a combination of two or more of the chemotherapeutic agents described herein, such as nanoparticle albumin bound paclitaxel, doxorubicin, and/or cyclophosphamide (NAC), can be tested in patients, such as patients with stages II-III HER-2 negative breast cancer. A series of studies are carried out with a combination of different chemotherapeutic agents. In each study, the period of providing a particular chemotherapeutic agent is different, for example, the particular chemotherapeutic agent is periodically administered to a patient at an interval of 1 day, 2 days, 3 days, 4 days, 5 days, 6 days, 7 days, 8 days, 9 days, or 10 days, or 1 week, 2 weeks, 3 weeks, or 4 weeks. The pCR for each study group is determined.

Likewise, the period of providing the second and/or third chemotherapeutic agent may be varied and the second and/or third chemotherapeutic agents may be administered simultaneously with, on the same day as, or on a different day as the first or second chemotherapeutic agent in order to identify a treatment regimen that provides desirable results. In addition, regimens in which, one or more of the chemotherapeutic agents are administered one or more times and the subsequent administrations of those chemotherapeutic agents discontinued while administration, of the remaining one or more chemotherapeutic agents is continued, may be evaluated to identify regimens that provide desirable results.

Using particular regimens, the pCR is at least 30%, 40, 50%, 60%, 70%, 80%, 90% or 95%. The optimum period for providing the particular chemotherapeutic agent in combination with at least one other chemotherapeutic agent is determined.

The above description discloses several compositions and methods of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

The following references are incorporated herein by reference in their entireties.

REFERENCES

1. American Cancer Society: Cancer Facts and FIGS. 2007. Atlanta: American Cancer Society; 2007.
2. Fisher B, Brown A, Mamounas E, Wieand S, Robidoux A, Margolese R G. Effect of preoperative chemotherapy on local-regional disease in women with operable breast cancer: findings from National Surgical Adjuvant Breast and Bowel Project B-18. J Clin Oncol. 1997 July; 15(7): 2483-93.

3. von Minckwitz G, Blohmer J U, Raab G, Löhr A, Gerber B. In vivo chemosensitivity-adapted preoperative chemotherapy in patients with early-stage breast cancer: the GEPARTRIO pilot study. Ann Oncol. 2005 January; 16(1):56-63.
4. Bear H D, Anderson S, Smith R E, Geyer C E Jr, Mamounas E P, Fisher B, Brown A M, Robidoux A, Margolese R, Kahlenberg M S, Paik S, Soran A, Wickerham D L, Wolmark N. Sequential preoperative or postoperative docetaxel added to preoperative doxorubicin plus cyclophosphamide for operable breast cancer: National Surgical Adjuvant Breast and Bowel Project Protocol B-27. J Clin Oncol. 2006 May 1; 24(13):2019-27.
5. Smith I C, Heys S D, Hutcheon A W, Miller I D, Payne S, Gilbert F J, Ah-See A K, Eremin O, Walker L G, Sarkar T K, Eggleton S P, Ogston K N. Neoadjuvant chemotherapy in breast cancer: significantly enhanced response with docetaxel. J Clin Oncol. 2002 March 15; 20(6):1456-66.
6. Mieog J S, van der Hage J A, van de Velde C J. Neoadjuvant chemotherapy for operable breast cancer. Br J Surg. 2007 October; 94(10):1189-200.
7. Norman Wolmark, M. D., "Preoperative Therapy in Invasive Breast Cancer: Reviewing the State of the Science and Exploring New Research Directions," National Cancer Institute, Natcher Conference Center, Bethesda, Md., Mar. 26-27, 2007.
8. van der Hage J A, van de Velde C J, Julien J P, Tubiana-Hulin M, Vandervelden C, Duchateau L. Preoperative chemotherapy in primary operable breast cancer: results from the European Organization for Research and Treatment of Cancer trial 10902. J Clin Oncol. 2001 November 15; 19(22):4224-37.
9. Wolmark N, Wang J, Mamounas E, Bryant J, Fisher B. Preoperative chemotherapy in patients with operable breast cancer: nine-year results from National Surgical Adjuvant Breast and Bowel Project B-18. J Natl Cancer Inst Monogr. 2001; (30):96-102.
10. Cleator S J, Makris A, Ashley S E, Lal R, Powles T J. Good clinical response of breast cancers to neoadjuvant chemoendocrine therapy is associated with improved overall survival. Ann Oncol. 2005 February; 16(2):267-72.
11. Semiglazov V F, Topuzov E E, Bavli J L, Moiseyenko V M, Ivanova O A, Seleznev I K, Orlov A A, Barash N Y, Golubeva O M, Chepic O F. Primary (neoadjuvant) chemotherapy and radiotherapy compared with primary radiotherapy alone in stage IIb-IIIa breast cancer. Ann Oncol. 1,994 September; 5(7):591-5.
12. Kaufmann M, Hortobagyi G N, Goldhirsch A, Scholl S, Makris A, Valagussa P, Blohmer J U, Eiermann W, Jackesz R, Jonat W, Lebeau A, Loibl S, Miller W, Seeber S, Semiglazov V, Smith R, Souchon R, Stearns V, Untch M, von Minckwitz G. Recommendations from an international expert panel on the use of neoadjuvant (primary) systemic treatment of operable breast cancer: an update. J Clin Oncol. 2006 April 20; 24(12):1940-9. Erratum in: J Clin Oncol. 2006 July 1; 24(19):3221.
13. Martin M, Pienkowski T, Mackey J, Pawlicki M, Guastalla J P, Weaver C, Adjuvant docetaxel for node-positive breast cancer. N Engl J Med. 2005 June 2; 352(22):2302-13.
14. G. Von Minckwitz, J. Blohmer, P. Vogel, C. Hanusch, H. Eidtmann, J. Hilfrich, B. Gerber, J. Huober, S. Costa and M. Kaufmann. Comparison of neoadjuvant 6 vs 8 cycles of docetaxel/doxorubicin/cyclophosphamide (TAC) in patients early responding to TACx2-the GEPARTRIO Study. Journal of Clinical Oncology, 2006 ASCO Annual Meeting Proceedings (Post-Meeting Edition). No 18S (June 20 Supplement), 2006: 576
15. Sledge G W, Neuberg D, Bernardo P, Ingle J N, Martino S, Rowinsky E K, Wood W C. Phase III trial of doxorubicin, paclitaxel, and the combination of doxorubicin and paclitaxel as front-line chemotherapy for metastatic breast cancer: an intergroup trial (E1193). J Clin Oncol. 2003 February 15; 21(4):588-92.
16. Mazouni C, Kau S W, Frye D, Andre F, Kuerer H M, Buchholz T A, Symmans W F, Anderson K, Hess K R, Gonzalez-Angulo A M, Hortobagyi G N, Buzdar A U, Pusztai L. Inclusion of taxanes, particularly weekly paclitaxel, in preoperative chemotherapy improves pathologic complete response rate in estrogen receptor-positive breast cancers. Ann Oncol. 2007 May; 18(5):874-80.
17. Desai N, Trieu V, Yao R, Labao E, Soon-Shiong P: Increased endothelial transcytosis of nanoparticle albumin-bound, paclitaxel (ABI-007) by gp60-receptors: a pathway inhibited, by taxol. 2004 SABCS. Abstract No. 1071.
18. Desai N, Trieu V, Yao R, Frankel T, Soon-Shiong P: SPARC expression in breast tumors may correlate to increased tumor distribution of nanoparticle albumin-bound paclitaxel (ABI-007) vs taxol. 2004 SABCS. Abstract No. 206.
19. Desai N, Trieu V, Yao Z, et al: Increased Antitumor Activity, Intratumor Paclitaxel Concentrations and Endothelial Cell Transport of Cremophor-Free, Albumin-Bound Paclitaxel, ABI-007, Compared with Cremophor-Based Paclitaxel. Clin Cancer Res. 2006; 12(4). 1317-1324.
20. Ibrahim N K, Desai N, Legha S, et al: Phase I and Pharmacokinetic Study of ABI-007, a Cremophor-free, Protein-stabilized, Nanoparticle Formulation of Paclitaxel. Clin Cancer Research. 2002 May; 8: 1038-1044
21. Ibrahim N K, Samuels B, Page R, et al: Multicenter Phase II Trial of ABI-007, an Albumin-Bound Paclitaxel, in Women with Metastatic Breast Cancer. J Clin Oncol 23:6019-6026, 2005.
22. Investigator's Brochure. ABRAXANE® (Paclitaxel Albumin Nanoparticle for Injectable Suspension) (ABI-007). American BioScience, Inc.
23. Gradishar W J, Tjulandin S, Davidson N, Shaw H, Desai N, Bhar P, Hawkins M, O'Shaughnessy J. Phase III trial of nanoparticle albumin-bound paclitaxel compared with polyethylated castor oil-based paclitaxel in women with breast cancer. J Clin Oncol. 2005 23(31):7794-803
24. Nyman D W, Campbell K J, Hersh, E, et al: Phase I and Pharmacokinetics Trial of ABI-007, a Novel Nanoparticle Formulation of Paclitaxel in Patients with Advanced Nonhematologic Malignancies. J Clin Oncol 23:7785-7793, 2005
25. Blum J L, et al: Long-term Disease Control in Taxane-Refractory Metastatic Breast Cancer Treated with nab paclitaxel. 2004 ASCO Annual Meeting Proceedings (Post-Meeting Edition). Vol 22, No 14S (July 15 Supplement), 2004: Abstract No. 543.
26. OShaughnessy J A, Blum J L, Sandbach J F, et al: Weekly Nanoparticle Albumin Paclitaxel (ABRAXANE®) Results in Long-Term Disease Control in Patients with Taxane-Refractory Metastatic Breast Cancer. 2004 SABCS. Abstract No. 1070
27. Robidoux A, Buyse M, Buzdar A, et al. Neoadjuvant chemotherapy with sequential weekly nanoparticle albumin-bound paclitaxel (ABI-007, ABRAXANE®) followed by 5-fluorouracil, epirubicin and cyclophosphamide (FEC) in locally advanced breast cancer (LABC): a phase II trial of the NSABP Foundation research programs (FRP) [poster]. Presented at: San Antonio Breast Cancer Symposium; Dec. 14-17, 2006; San Antonio, Tex. Abs 3068.

28. Gradishar W, Krasnojon D, Cheporov S, et al. Randomized comparison of weekly or every-3-week (q3w) nab-paclitaxel compared to q3w docetaxel as first-line therapy in patients (pts) with metastatic breast cancer (MBC). J Clin Oncol, 2007 ASCO Annual Meeting Proceedings. 25 (18S) (June 20 Supplement), 2007: 1032

What is claimed is:

1. A method of treating a HER2 negative breast cancer in a subject in need thereof comprising:
    administering a chemotherapeutic agent associated with or bound to albumin, wherein the chemotherapeutic agent associated with or bound to albumin comprises a taxane;
    administering a second chemotherapeutic agent comprising a topoisomerase inhibitor; and
    administering a third chemotherapeutic agent comprising an alkylating agent,
    wherein the chemotherapeutic agent associated with or bound to albumin, the second chemotherapeutic agent comprising a topoisomerase inhibitor, and the third chemotherapeutic comprising an alkylating agent are administered on the same day.

2. The method of claim 1, wherein administration of the chemotherapeutic agent associated with or bound to albumin is repeated.

3. The method of claim 1, wherein administration of the second chemotherapeutic agent and the third chemotherapeutic agent is not repeated.

4. The method of claim 1, wherein the chemotherapeutic agent associated with or bound to albumin comprises an agent selected from the group consisting of paclitaxel, and docetaxel.

5. The method of claim 1, wherein the chemotherapeutic agent associated with or bound to albumin comprises nab-paclitaxel.

6. The method of claim 1, wherein the topoisomerase inhibitor is doxorubicin.

7. The method of claim 1, wherein the alkylating agent is cyclophosphamide.

8. The method of claim 1, wherein the chemotherapeutic agent associated with or bound to albumin is administered on days 1 and 8.

9. The method of claim 1, wherein the chemotherapeutic agent associated with or bound to albumin is administered on days 1, 8, and 15.

10. The method of claim 1, wherein the chemotherapeutic agent associated with or bound to albumin is administered on days 1, 8, and 22.

11. The method of claim 1, wherein the chemotherapeutic agent associated with or bound to albumin is administered at an interval of at least 5 days.

12. The method of claim 2, wherein the administration of the chemotherapeutic agent associated with or bound to albumin is repeated at least twice.

13. The method of claim 1, wherein administration of the chemotherapeutic agent associated with or bound to albumin is repeated with an interval of at least 5 days.

14. The method of claim 1, wherein:
    the chemotherapeutic agent associated with or bound to albumin comprises nab-paclitaxel,
    the second chemotherapeutic agent comprises doxorubicin, and
    the third chemotherapeutic agent comprises cyclophosphamide; and
    at least about 100 mg/m$^2$ nab-paclitaxel is administered on day 1 and 8, at least about 50 mg/m$^2$ doxorubicin is administered on day 1, and at least about 500 mg/m$^2$ cyclophosphamide is administered on day 1.

15. The method of claim 14, further comprising administering pegfilgrastim on day 9.

16. The method of claim 1, wherein the breast cancer is triple negative breast cancer.

17. The method of claim 5, wherein the administered dose of nab-paclitaxel is between about 50 mg/m$^2$ and about 200 mg/m$^2$.

18. The method of claim 5, wherein the administered dose of nab-paclitaxel is selected from the group consisting of 100 mg/m$^2$ and 150 mg/m$^2$.

19. The method of claim 1, wherein the taxane is selected from the group consisting of cabazitaxel, docetaxel, larotaxel, ortataxel, paclitaxel, and tesetaxel.

20. The method of claim 1, wherein the topoisomerase inhibitor is selected from the group consisting of camptothecin, topotecan, irinotecan, rubitecan, belotecan, etoposide, teniposide, aclarubicin, daunorubicin, doxorubicin, epirubicin, idarubicin, amrubicin, pirarubicin, valrubicin, zorubicin, mitoxantrone, and pixantrone.

21. The method of claim 1, wherein the alkylating agent is selected from the group consisting of mechlorethamine, cyclophosphamide, ifosfamide, trofosfamide, chlorambucil, melphalan, prednimustine, bendamustine, uramustine, carmustine, lomustine, fotemustine, nimustine, ranimustine, streptozocin, busulfan, mannosulfan, treosulfan, carboquone, N,N'N'-triethylenethiophosphoramide (thioTEPA), triaziquone, and triethylenemelamine.

22. The method of claim 1, wherein the breast cancer is an estrogen receptor positive (ER+) breast cancer.

* * * * *